US00PP22778P3

(12) United States Plant Patent
Wright et al.

(10) Patent No.: US PP22,778 P3
(45) Date of Patent: Jun. 12, 2012

(54) BLUEBERRY PLANT NAMED 'C00-09'

(50) Latin Name: ***Vaccinium* hybrid**
Varietal Denomination: C00-09

(75) Inventors: Gary Wright, Corindi Beach (AU); Paul Lyrene, Micanopy, FL (US)

(73) Assignees: CostaExchange Ltd., Ravenhill (AU); Florida Foundation Seed Producers, Inc., Gainesville, FL (US)

( * ) Notice: Subject to any disclaimer, the term of this patent is extended or adjusted under 35 U.S.C. 154(b) by 0 days.

(21) Appl. No.: 12/802,255

(22) Filed: Jun. 1, 2010

(65) Prior Publication Data

US 2010/0313314 P1 Dec. 9, 2010

Related U.S. Application Data

(60) Provisional application No. 61/217,855, filed on Jun. 5, 2009.

(51) Int. Cl.
*A01H 5/00* (2006.01)

(52) U.S. Cl. ..... Plt./157

(58) Field of Classification Search ..... Plt./157
See application file for complete search history.

*Primary Examiner* — June Hwu

(74) *Attorney, Agent, or Firm* — Davis Wright Tremaine LLP; Dale C. Hunt

(57) ABSTRACT

A new and distinct cultivar of blueberry (*Vaccinium* hybrid) plant named 'C00-09', characterized by its combination of upright to bushy plant shape and strong plant growth vigor, evergreen foliage with late timing of vegetative bud burst, lateness of flowering and fruiting, large to very large fruit size with oblate shape, firm fruit suited to handling, attractive dark blue fruit color and small picking scar, strong berry sweetness with weak to medium acidity. This combination results in higher quality fruit with a later availability than other varieties.

2 Drawing Sheets

Latin name of genus and species of plant claimed: *Vaccinium* hybrid.

Variety denomination: 'C00-09'.

BACKGROUND OF THE INVENTION

The present invention relates to a new and distinct perennial variety of *Vaccinium* hybrid (Southern Highbush Blueberry), which has been given the variety denomination of 'C00-09'. Its market class is that of a fruiting plant. 'C00-09' is intended for use as fresh fruit for shipping, customer pick and processing markets and as a home garden plant.

The new blueberry cultivar is a selection resulting from seedlings produced in a controlled breeding programme of *Vaccinium* at Gainesville, Fla., USA in 1998 from a cross of seed parent "F92-52" (unpatented) and pollen parent "F84-38" (unpatented). The new cultivar was discovered and selected as a single plant within a population of blueberry plants in 2000 in a commercial field plantation environment at Corindi Beach, New South Wales, Australia. Selection criteria was a combination of upright to bushy plant shape and strong plant growth vigor, evergreen foliage, lateness of flowering and fruiting, large fruit size, firm fruit suited to handling, attractive dark blue fruit color and small picking scar. The selection was subsequently evaluated for a number of years at the commercial farms at Corindi Beach, New South Wales, Australia.

Asexual reproduction of the new cultivar by cutting propagation since 2000 at Corindi Beach, New South Wales, Australia and has demonstrated that the new cultivar reproduces true to type with all of the characteristics, as herein described, firmly fixed and retained through successive generations of such asexual propagation.

The new variety has been primarily compared to the variety 'Southern Belle' (U.S. Plant Pat. No. 13,931). In Corindi Beach, New South Wales, Australia the plant growth habit of 'C00-09' is 'upright to bushy' whereas the plant growth habit of 'Southern Belle' is 'upright'. The plant growth vigor of 'C00-09' is 'strong' whereas the plant growth vigor of 'Southern Belle' is 'weak to medium'. The leaf length of 'C00-09' is 'long' (65-70 mm) whereas the leaf length of 'Southern Belle' is 'medium to long' (mean 57 mm). The leaf width of 'C00-09' is 'broad' (30-35 mm) whereas the leaf width of 'Southern Belle' is 'medium' (mean 28 mm). The fully developed leaf attitude of 'C00-09' is usually 'horizontal' whereas the fully developed leaf attitude of 'Southern Belle' is 'acute'. The width of the corolla tube on a flower of 'C00-09' is 'medium to broad' (11-12 mm) whereas the width of the corolla tube on a flower of 'Southern Belle' is 'narrow to medium' (8-9 mm). The berry diameter of 'C00-09' is 'large to very large' (mean 24 mm) whereas the berry diameter of 'Southern Belle' is 'large' (mean 19 mm). The mean berry weight of 'C00-09' was found to be 5.0 grams whereas the mean berry weight of 'Southern Belle' was found to be 2.8 grams. The depth of the calyx basin on a berry of 'C00-09' is deep whereas the depth of the calyx basin on a berry of 'Southern Belle' is 'medium'. The diameter of the calyx basin on a berry of 'C00-09' is 'broad' (mean 7.6 mm) whereas the diameter of the calyx basin on a berry of 'Southern Belle' is 'medium' (mean 4.9 mm). The sweetness of a berry of 'C00-09' is classified as 'strong' whereas the sweetness of a berry of 'Southern Belle' is classified as 'weak'. The acidity of a berry of 'C00-09' is classified as 'weak to medium' whereas the acidity of a berry of 'Southern Belle' is classified as 'weak'. This combination of fruiting attributes results in 'C00-09' being a more suitable variety for commercial and home garden use than 'Southern Belle'.

SUMMARY OF THE INVENTION

The following characteristics of the new cultivar have been repeatedly observed and can be used to distinguish 'C00-09' as a new and distinct cultivar of blueberry plant:

1. Upright to bushy plant growth habit
4. Late timing of fruit ripening
5. Dark blue berry color
6. Berry firmness is firm
7. Picking scar is dry
8. Berry Diameter is large to very large
9. Berry shape is longitudinal cross-section is oblate
10. Berry sweetness is strong
11. Berry acidity is weak to medium Plants of the new cultivar differ from plants of the parents primarily in spreading growth late timing of beginning of flowering, late timing of berry ripening, and larger to very large berry diameter, whereas the parent varieties are mid-season in timing of flowering and berry ripening with medium berry diameters.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'C00-09'.

DETAILED BOTANICAL DESCRIPTION

Figure 1:
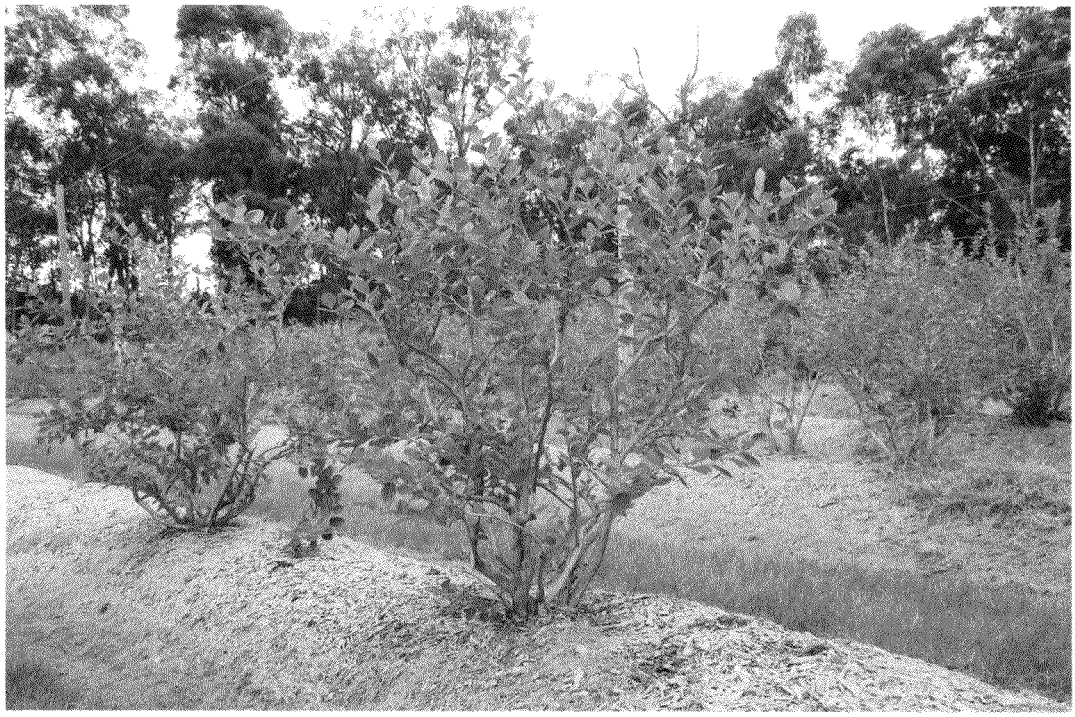
FIG. 1 illustrates a 'C00-09' plant in a commercial field planting.
Figure 2:
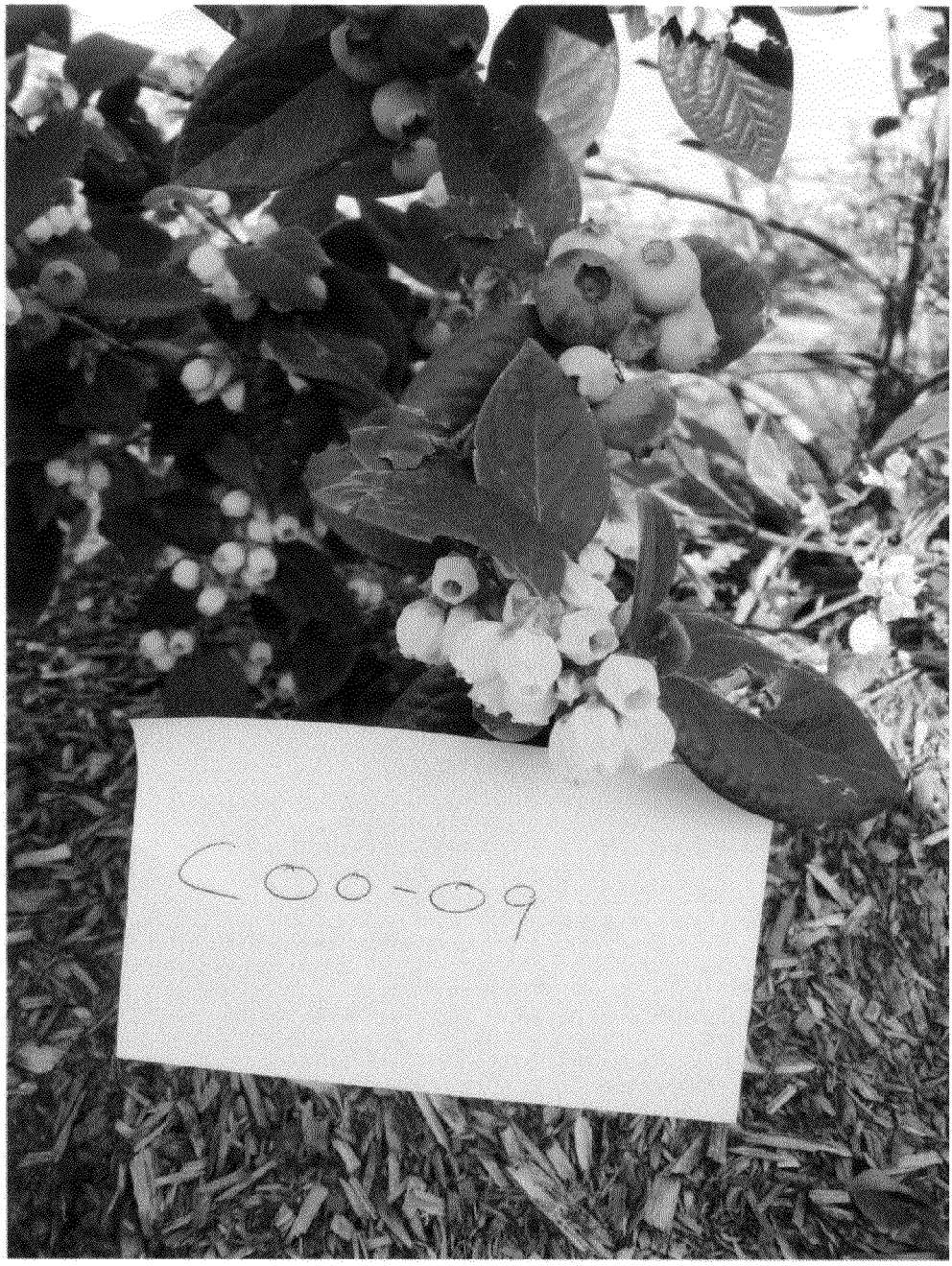
FIG. 2 illustrates C00-09 flowering and fruiting branch.

The following is a detailed botanical description of a new and distinct variety of a *Vaccinium* hybrid ornamental plant known as 'C00-09'. Plant observations were made on plants grown in Corindi Beach, New South Wales, Australia. Unless indicated otherwise, the descriptions disclosed herein are based upon observations made from August to October 2007 of mature 'C00-09' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'C00-09' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Vaccinium* hybrid cultivar C00-09.

Parentage:

*Parents*.—Seed parent "F92-52" (unpatented) and pollen parent "F 84-38" (unpatented).

Plant:

*Growth habit*.—Plants are upright to bushy. Growth vigor is strong. Plant height is 1.9 m. Plant width is 1.2 m. Flower bud density is medium. Twigginess is low. Time of beginning of leaf bud burst is late (mid September) when grown as an evergreen in Australia. Time of beginning of flowering is early late (early September) when grown as an evergreen in Australia. Time of fruit ripening is late (mid-late October) when grown as an evergreen in Australia. Self-fruitfulness is moderate and interplanting with another cultivar for cross-pollination is advised.

Stem:

*Suckering tendency*.—Plants typically have 5-7 major canes per plant from a base 30 cm in diameter on 6 year old plants.

*Canes*.—Erect to semi-erect with moderate branching; color greyed green 198C; 2 year old cane diameter 12 mm, colored greyed orange 177B, some flaking of bark, current season wood diameter 3-4 mm, colored yellow green 144C.

*Internode length on strong, new shoots*.—15-20 mm.

*Fruiting wood*.—Numerous twigs to 10 cm in length.

*Surface texture of new wood*.—Smooth.

*Petiole*.—Color yellow green 154D. Average length of 1-2 mm long.

*Surface texture*.—Smooth to slightly pubescent.

Fully developed leaf:

*Length*.—Medium 65-70 mm.

*Width*.—Broad approximately 30-35 mm.

*Shape*.—Elliptic.

*Color*.—Yellow green 137A.

*Intensity of color*.—Medium.

*Margin*.—Entire.

*Undulation of margin*.—Absent or very weak.

*Pubescence of upper side*.—Absent.

*Pubescence of lower side*.—Absent.

*Cross sectional profile*.—Flat.

*Longitudinal profile*.—Straight.

*Attitude*.—Horizontal.

Inflorescence:

*Average size*.—45 mm long by 25 mm wide.

*Length of peduncle*.—To 12 mm.

*Surface texture of peduncle*.—Smooth.

*Peduncle color*.—144D.

*Length of pedicel*.—Very long 7-9 mm.

*Surface texture of pedicel*.—Smooth.

*Pedicel color*.—144C.

*Number of flowers per cluster*.—Median 7.

*Flower cluster density*.—Is medium.

*Flower arrangement*.—Is racemose, fasciculate (2 to 3 flowers) or solitary.

Flowers:

*Length of corolla tube*.—Medium-long (to 16 mm).

*Width of corolla tube*.—Medium-broad (to 12 mm).

*Corolla aperture diameter*.—4 mm.

*Color of corolla*.—White 155D.

*Anthocyanin coloration of corolla*.—Absent or very weak.

*Corolla ridges*.—Present.

*Protrusion of stigma*.—Absent.

*Fragrance*.—Weak.

*Shape*.—Urceolate.

*Abundance of pollen*.—High.

*Color of pollen*.—White to yellow white 158D.

*Calyx (with sepals) diameter*.—5-6 mm.

*Calyx color*.—Green 138A.

Market class: Suitable for the commercial, hand harvest fresh, processed, and home garden markets.

Productivity: 3 to 4 kg per season from 3-4 year old plants planted at 3.0 m×0.9 m density; yield was recorded on 4-year old plants growing in a deep, light-texture soil in Corindi, NSW. C97-41 produced 7.0 lb/plant (=3.2 kg/plant).

Cold hardiness: 'C00-09' has not been grown in all environments including harsh winter environments. Cold tolerance is expected to be low. Plants have survived winter freeze in Australia to minus 8° C. with minimal winter dieback of young shoots and resultant loss of fruit and flowers, and poor growth vigor.

Chilling requirement: 'C00-09' has not been grown in all environments and is typically grown as an evergreen crop where chilling hours are not important. 'C00-09' is classed as 'low chill', typical of Southern Highbush Blueberry varieties with an estimated chilling requirement of 250 hours (not tested).

Leafing: Plants retain leaves year round (at Corindi beach, NSW Australia) and 'C00-09' is grown commercially as an evergreen crop. New leafing occurs in mid September at Corindi beach, NSW Australia.

Fruit:

*Unripe fruit color intensity*.—Medium.
*Unripe fruit color*.—144A.
*Cluster density*.—Is medium.
*Diameter*.—Is large to very large (mean 23.6 mm).
*Weight*.—Heavy (approximately 5.3 g).
*Shape*.—Oblate.
*Attitude of calyx*.—Erect.
*Diameter of calyx basin*.—Broad (mean 7.6 mm).
*Depth of calyx basin*.—Is deep (to 2.5 mm).
*Intensity of bloom*.—Strong Intensity of blue color of skin with bloom removed is very dark.
*Color of skin*.—202A.
*Sweetness when ripe*.—Strong.
*Firmness when ripe*.—Firm.
*Acidity when ripe*.—Weak to medium.
*Size of scar*.—Is small (1.0-1.5 mm).
*Storage quality*.—Good.
*Color of flesh*.—Yellow green 145D to yellow green 150D.

Date of 50% maturity: Approximately 20$^{th}$ October at Corindi beach, NSW Australia.

Fruit development period: Approximately 50 days in protected cultivation at Corindi beach, NSW Australia.

Seed:

*Seed color*.—Greyed orange 165B.
*Seed abundance in fruit*.—Medium.
*Seed size*.—1.6-1.8 mm long for fully developed seeds. Average of 48 seeds per Berry.

Tolerance to disease: 'C00-09' has shown moderate resistance to root disease (*Phytophthora* spp) and good resistance to blueberry rust compared to the commercial variety Southern Belle. Also demonstrates good resistance to the fruit disease Anthracnose (*Colletotrichum gleosporoides*).

What is claimed is:

1. A new and distinct cultivar of blueberry plant named 'C00-09', substantially as herein shown and described.

* * * * *